(12) United States Patent
Lovett

(10) Patent No.: US 7,177,682 B2
(45) Date of Patent: Feb. 13, 2007

(54) HIGHLY SPECIFIC TECHNIQUE FOR DISCRIMINATING ATRIAL FIBRILLATION FROM ATRIAL FLUTTER

(75) Inventor: Eric G. Lovett, Roseville, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 816 days.

(21) Appl. No.: 10/218,944

(22) Filed: Aug. 13, 2002

(65) Prior Publication Data

US 2002/0193838 A1 Dec. 19, 2002

Related U.S. Application Data

(62) Division of application No. 09/548,981, filed on Apr. 14, 2000, now Pat. No. 6,496,731.

(51) Int. Cl.
  *A61N 1/362* (2006.01)
  *A61B 5/046* (2006.01)
(52) U.S. Cl. ............... 607/14; 607/3; 607/4; 600/518
(58) Field of Classification Search ............ 607/3, 607/4, 5, 14; 600/515, 516, 518, 519, 521
  See application file for complete search history.

(56) References Cited

U.S. PATENT DOCUMENTS

| | | | |
|---|---|---|---|
| 3,648,688 A | 3/1972 | O'Hanion, Jr. et al. | 128/2.06 A |
| 3,699,949 A | 10/1972 | O'Hanion, Jr. et al. | 128/2.06 A |
| 4,018,219 A | 4/1977 | Hojaiban | 128/2.06 A |
| 4,830,006 A * | 5/1989 | Haluska et al. | 607/4 |
| 5,191,524 A | 3/1993 | Pincus et al. | 364/413.05 |
| 5,285,793 A | 2/1994 | Slovut et al. | 128/706 |
| 5,330,505 A * | 7/1994 | Cohen | 607/6 |
| 5,379,776 A | 1/1995 | Murphy et al. | 128/705 |
| 5,411,031 A | 5/1995 | Yomtov | 128/706 |
| 5,591,215 A | 1/1997 | Greenhut et al. | 607/14 |
| 5,682,901 A | 11/1997 | Kamen | 128/706 |
| 5,720,295 A | 2/1998 | Greenhut et al. | 600/517 |
| 5,730,141 A | 3/1998 | Fain et al. | 128/705 |
| 5,772,604 A | 6/1998 | Langberg et al. | 600/518 |
| 5,782,876 A | 7/1998 | Flammang | 607/4 |
| 5,814,081 A | 9/1998 | Ayers et al. | 607/5 |
| 5,879,295 A | 3/1999 | Li et al. | 600/373 |
| 5,916,239 A | 6/1999 | Geddes et al. | 607/14 |
| 5,968,079 A | 10/1999 | Warman et al. | 607/5 |
| 5,991,660 A | 11/1999 | Goyal | 607/14 |

\* cited by examiner

*Primary Examiner*—Kennedy Schaetzle
(74) *Attorney, Agent, or Firm*—Schwegman, Lundberg, Woessner, & Kluth

(57) ABSTRACT

A cardiac rhythm management system including a highly sensitive technique for discriminating AF from AFL. An electrode disposed in or about a heart senses a cardiac signal. A controller through a sensing circuit receives the sensed cardiac signal from the electrode and processes the sensed cardiac signal to compute an average cycle length-to-cycle length variation based on serial interval relationships from the sensed cardiac signal, and then comparing the computed average cycle length-to-cycle length variation to one or more pre-determined threshold values to discriminate AF from AFL. As a result of substantial difference in cycle length-to-cycle length variation between AF and AFL (despite similar average cycle lengths), the sequence-based measure of cycle length-to-cycle length variability proves to be a highly specific and reliable discriminator of AF from AFL.

19 Claims, 10 Drawing Sheets

HIGHLY SPECIFIC TECHNIQUE FOR DISCRIMINATING ATRIAL FIBRILLATION FROM ATRIAL FLUTTER

CROSS-REFERENCE TO RELATED APPLICATION(S)

This patent application is a division of U.S. patent application Ser. No. 09/548,981, filed on Apr. 14, 2000, now issued as U.S. Pat. No. 6,496,731, the specification of which is incorporated herein by reference in its entirety.

TECHNICAL FIELD

This invention relates generally to cardiac rhythm management systems, and particularly, but not by way of limitation, to a system for detecting atrial fibrillation and for discriminating atrial fibrillation from atrial flutter.

BACKGROUND

When functioning properly, the human heart maintains its own intrinsic rhythm, and is capable of pumping adequate blood throughout the body's circulatory system. The body's autonomic nervous system regulates intrinsic electrical heart activity signals that are conducted to atrial and ventricular heart chambers on the left and right sides of the heart. The electrical heart activity signals trigger resulting heart contractions that pump blood. However, some people have irregular cardiac rhythms, referred to as arrhythmias. Some of the most common arrhythmias are atrial fibrillation (AF) and atrial flutter (AFL). Atrial fibrillation can result in significant patient discomfort and even death because of number of associated problems, including: (1) an irregular heart rate which causes the patient discomfort and anxiety, (2) loss of synchronous atrioventricular contractions which interferes with cardiac hemodynamics, resulting in varying levels of congestive heart failure, and (3) stasis of blood flow, which increases the vulnerability to thromboembolism. AF most commonly exhibit heartbeat rates of about 400 to 600 per minute in humans. On the other hand AFL is characterized by approximately 250 to 300 beats per minute. AFL is thought to result from a counterclockwise reentry circuit in the right atrium associated with the atrial septum and the right atrial freewall. The reentry circuit normally travels between the inferior vena cava and the tricuspid valve. Overlap between the ranges of number of beats per minute in AF and AFL is not uncommon.

One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of cardiac rhythm management system. Such a system may be implanted in a patient to deliver therapy to their heart.

Cardiac rhythm management systems include, among other things, implanted rhythm management devices. Implanted rhythm management devices deliver, among other things, timed sequences of low energy electrical stimuli, called pace pulses, to the heart, such as via a transvenous lead wire or catheter (referred to as a "lead") having one or more electrodes disposed in or about the heart. Heart contractions are initiated in response to such pace pulses (this is referred to as "capturing" the paced heart). By properly timing the delivery of pace pulses, the heart can be induced to contract in proper rhythm, greatly improving its efficiency as a pump. Such devices are often used to treat patient's hearts exhibiting arrhythmias. Implanted rhythm management devices is also used to deliver high-energy defibrillation pulses via lead wire having one or more electrodes disposed in or about the heart for providing defibrillation therapy.

Implanted rhythm management devices generally include sensing circuits to sense electrical signals from a heart tissue in contact with the electrodes. Then a controller in the implanted rhythm management device processes these signals and issues command signals to therapy circuits, for delivery of electrical energy such as pacing and/or defibrillation pulses to the appropriate electrodes in or about the heart to provide therapy to the heart. The controller may include a microprocessor or other controller for execution of software and/or firmware instructions. The software of controller may be modified to provide different parameters, modes, and/or functions for the implantable device to adapt or improve performance of the device. Generally algorithms are used in software and/or firmware residing in the controller to discriminate sensed signals and to provide appropriate therapy to the heart. Algorithms are also used to discriminate AF from AFL. In general, AF exhibits shorter cycle lengths (CLs) and greater cycle length (CL) variability than AFL. Current techniques are based on interval information and ignore serial interval relationships. Thus, there is a need for a more reliable, more sensitive and less computationally oriented method of detection of AF and discrimination from AFL in implanted rhythm management devices to provide the appropriate therapy to the heart and to reduce patient morbidity and discomfort.

SUMMARY

The above-mentioned shortcomings, disadvantages and problems are addressed by the present invention, which will be understood by reading and studying the following specification. The present system provides, among other things, a reliable technique for discriminating atrial fibrillation (AF) from atrial flutter (AFL). The present technique allows for reduced computation and increased sensitivity and specificity in discriminating between AF and AFL.

According to one aspect of the present subject matter, a sensor disposed in or about a heart, senses a cardiac signal. A controller through a sensing circuit then receives the sensed cardiac signal. The controller processes the cardiac signal to discriminate AF from AFL, by computing average cycle length-to-cycle length variability (high frequency variability of cycle lengths) between adjacent cycle lengths for a pre-determined number of sequential cycle lengths, and comparing the computed high frequency variability, with one or more pre-determined threshold values, to discriminate AF from AFL, and issue a command signal to a therapy circuit based on the outcome of the comparison. Then the controller provides the appropriate therapy to the heart through an electrode disposed in or about the heart. As a result of using such a sequence-based algorithm, the system is generally capable of providing a superior performance over existing algorithms in discriminating AF from AFL, which neglect any serial cycle length properties. Current algorithms based on interval techniques rely on sequence-independent measures of atrial interval dispersion (e.g., standard deviation, range, local extrema, etc.,) to differentiate the relatively fixed cycle length of AFL from the relatively large cycle-to-cycle variability characteristic of AF. Viewed in the interval domain, AFL presents a constant or slowly changing (low frequency) cycle length, while AF exhibits large intercycle duration variations (high frequency activity). The present invention consists of a measure of average cycle length-to-cycle length variability (in the interval sense) for a given interval sequence. With the substantial difference in high frequency activity between AF and AFL (despite similar average cycle lengths), the sequence based measure of average high frequency variability will prove to be a highly specific discriminator when robust atrial interval sequences are available. The algorithm may also prove useful in discriminating certain ventricular tachycardias from ventricular fibrillation. In one embodiment, the comparator compares the average cycle length with the average cycle length-to-cycle length variation, and issues a command signal based on the outcome of the comparison. In another embodiment the comparator compares the central tendency (e.g., mean, median or mode) cycle length-to-cycle length variation, and issues a command signal based on the outcome of the comparison. In one embodiment the comparator further classifies the computed average cycle length-to-cycle length variation to detect a cardiac arrhythmia.

In one embodiment, the electrode is disposed in and/or around an atrial region of a heart to sense a cardiac signal around an atrial chamber. In one embodiment, the electrode is disposed in and/or around a ventricular region of the heart to sense the cardiac signal. In another embodiment, a therapy includes providing pacing pulse electrical energy, when AFL is detected by the controller. In another embodiment, the therapy includes providing defibrillation pulse electrical energy when AF is detected by the controller. In another embodiment, the therapy includes activating an implanted or external device to administer a drug therapy when controller detects AF or AFL. In another embodiment, an external programmer, remote from an implanted cardiac rhythm management system, is used to communicate with the controller and to program the controller. In one embodiment a timer is included to introduce a delay between receiving the command signal from the comparator and administering the drug therapy to the heart. Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

Figure 1:
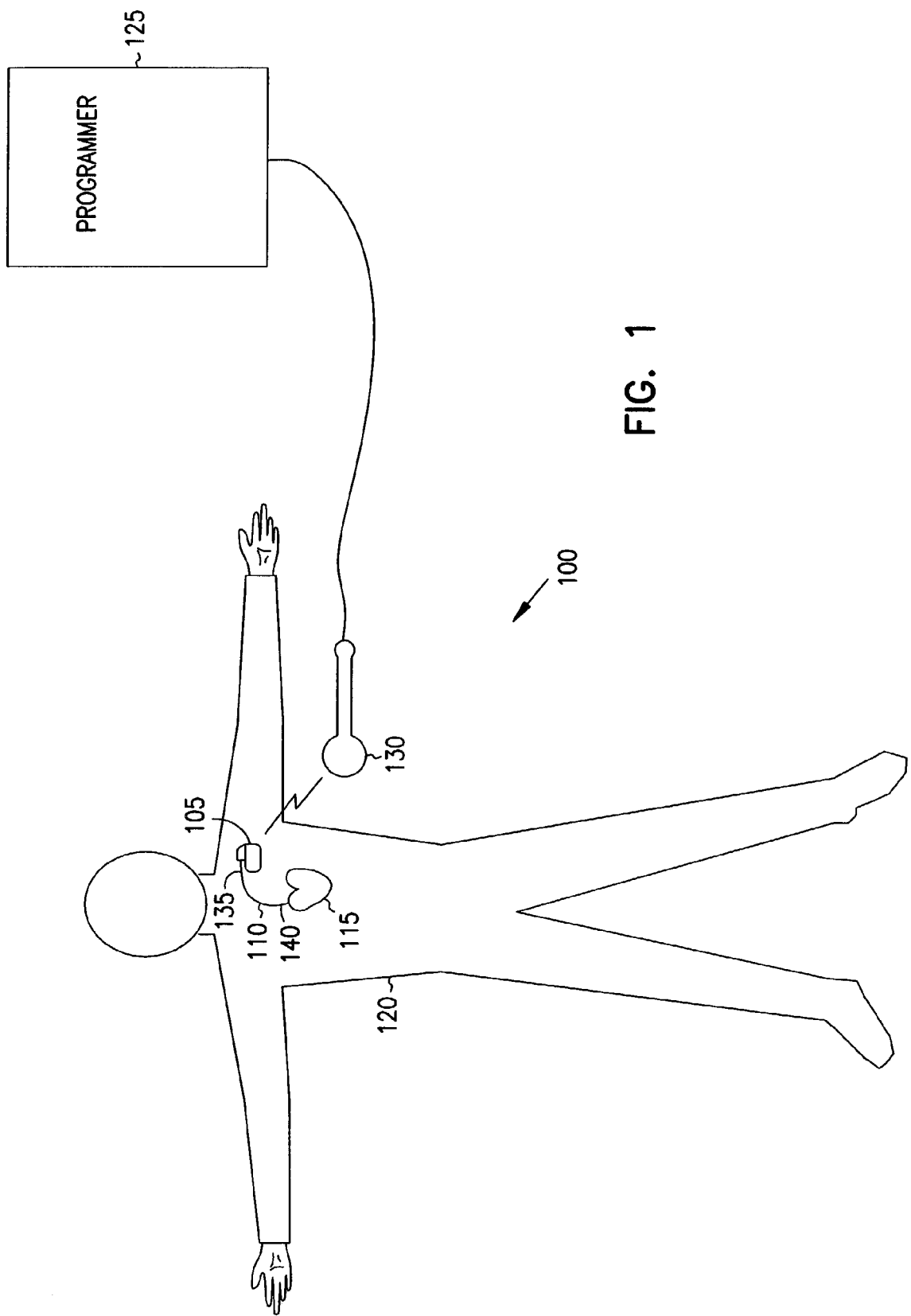
FIG. 1 is a schematic/block diagram illustrating generally one embodiment of portions of a cardiac rhythm management system and an environment in which it is used.

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different suffixes represent different instances of substantially similar components.

In this document, the term cycle length ($\Delta t_1, \Delta t_2 \ldots \Delta t_N$) is understood to refer to the time between two adjacent activations of a heart. The term average cycle length ($1/N (\Sigma \Delta t_1 + \Delta t_2 \ldots + \Delta t_N)$) is understood to refer to an average of all of the cycle lengths computed over a pre-determined interval sequence. Furthermore, the term average cycle length-to-cycle length variability (average high frequency variability) (($1/(N-1)$) ($\Sigma(|\Delta t_1 - \Delta t_2| + |\Delta t_2 - \Delta t_3| \ldots + |\Delta t_{N-1} - \Delta t_N|$))) is understood to refer to an average of the difference in time between adjacent cycle lengths (activation-to-activation interval variability) of the heart over a pre-determined interval sequence. Furthermore the term 'central tendency' is understood to refer to median, mean, mode, or average.

General System Overview

This document describes, among other things, a cardiac management system for discriminating AF from AFL from detected atrial arrhythmia. The present system has an improved specificity in discriminating AF from AFL signals, because of using an algorithm that uses a serial interval relationship to discriminate atrial fibrillation from atrial flutter from the sensed cardiac signals. The system is also capable of providing a superior performance over existing algorithms. Current algorithms based on interval techniques rely on sequence-independent measures of atrial interval dispersion (e.g., standard deviation, range, local extrema, etc.,) to differentiate the relatively fixed cycle length of AFL from the large cycle-to-cycle variability characteristic of AF. Viewed in the interval domain, AFL presents a constant or slowly changing (low frequency) cycle length, while AF exhibits large intercycle duration variations (high frequency activity). The present invention consists of a measure of average high frequency variability (in the interval sense) for a given interval sequence. With the substantial difference in high frequency activity between AF and AFL (despite similar average cycle lengths), the sequence based measure of average high frequency variability will prove to be a highly specific discriminator when robust atrial interval sequences are available. Similarly, the algorithm may also prove useful in discriminating certain ventricular tachycardias from ventricular fibrillation. Other aspects of the invention will be apparent on reading the following detailed description of the invention and viewing the drawings that form a part thereof.

FIG. 1 is a schematic/block diagram illustrating generally, by way of example, but not by way of limitation, one embodiment of portions of a cardiac rhythm management system 100 and an environment in which it is used. In FIG. 1, system 100 includes an implantable cardiac rhythm management device 105, also referred to as an electronics unit, which is coupled by an intravascular endocardial lead 110, or other lead, to a heart 115 of a patient 120. System 100 also includes an external programmer 125 providing wireless communication with device 105 using a telemetry device 130. Catheter lead 110 includes a proximal end 135, which is coupled to a device 105, and a distal end 140, which is coupled to one or more portions of the heart 115.

Figure 2:
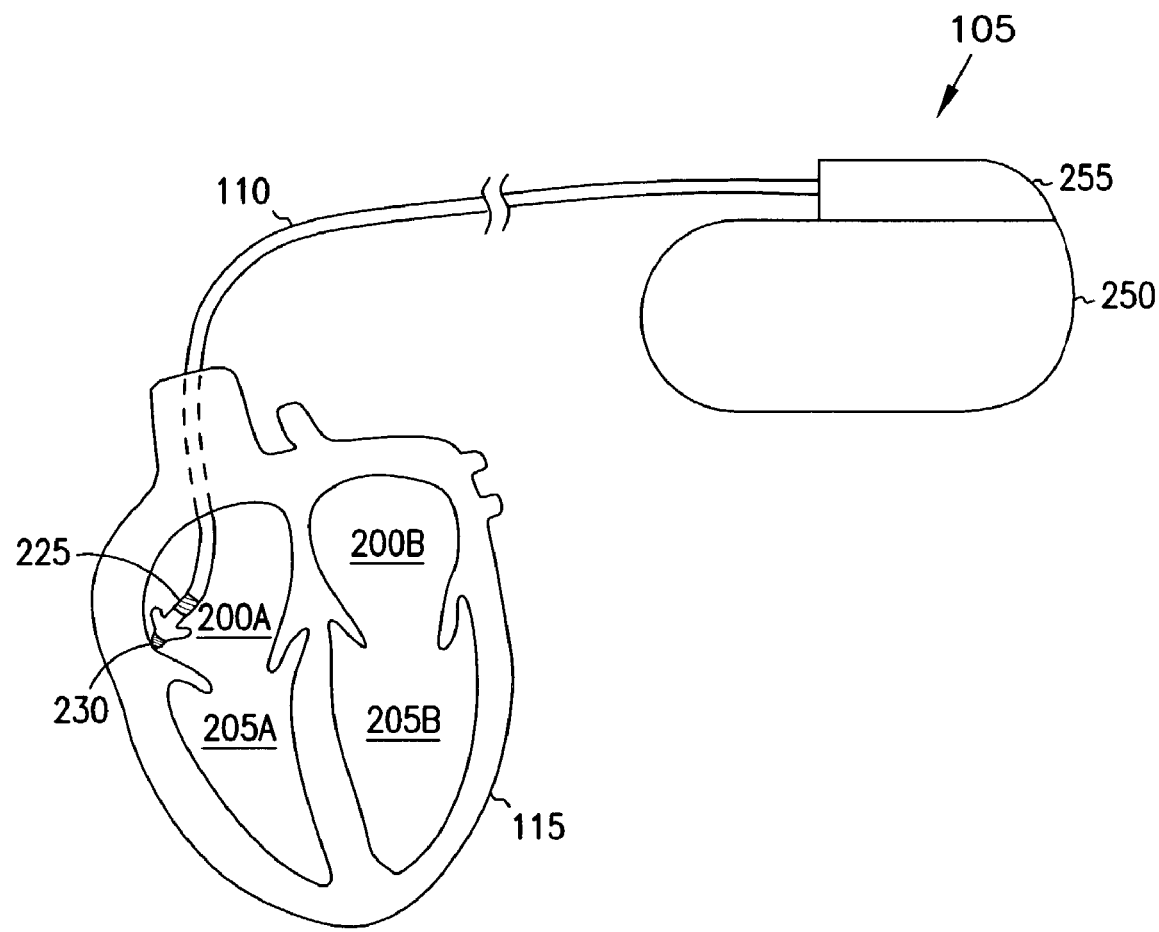
FIG. 2 is a schematic drawing illustrating generally one embodiment of portions of a cardiac rhythm management system coupled to a heart by a right atrial electrode.

FIG. 2 is a schematic/block diagram illustrating, by way of example, but not by way of limitation, one embodiment of device 105 coupled by an atrial lead 110 to a heart 115, which includes a right atrium 200A, a left atrium 200B, a right ventricle 205A, and a left ventricle 205B. In this embodiment, lead 110 includes electrodes (electrical contacts) disposed in, around, or near a right atrium 200A of the heart 115, such as a ring electrode 225 and tip electrode 230, for sensing signals and/or delivering therapy to the heart's right atrium 200A. Alternatively lead 110 could include an electrode disposed in, around, or near a right ventricle 205A of the heart 115, for sensing signals and/or delivering therapy to the heart's right ventricle 205A. Lead 110 optionally also includes additional electrodes, such as for delivering atrial and/or ventricular cardioversion/defibrillation and/or pacing therapy to the heart 115. Device 105 includes components that are enclosed in a hermetically-sealed can 250. Additional electrodes may be located on the can 250, or on an insulating header 255, or on other portions of device 105, for providing unipolar pacing and/or defibrillation energy in conjunction with the electrodes disposed in or around heart 115.

Example Implanted Rhythm Management Device

Figure 3:
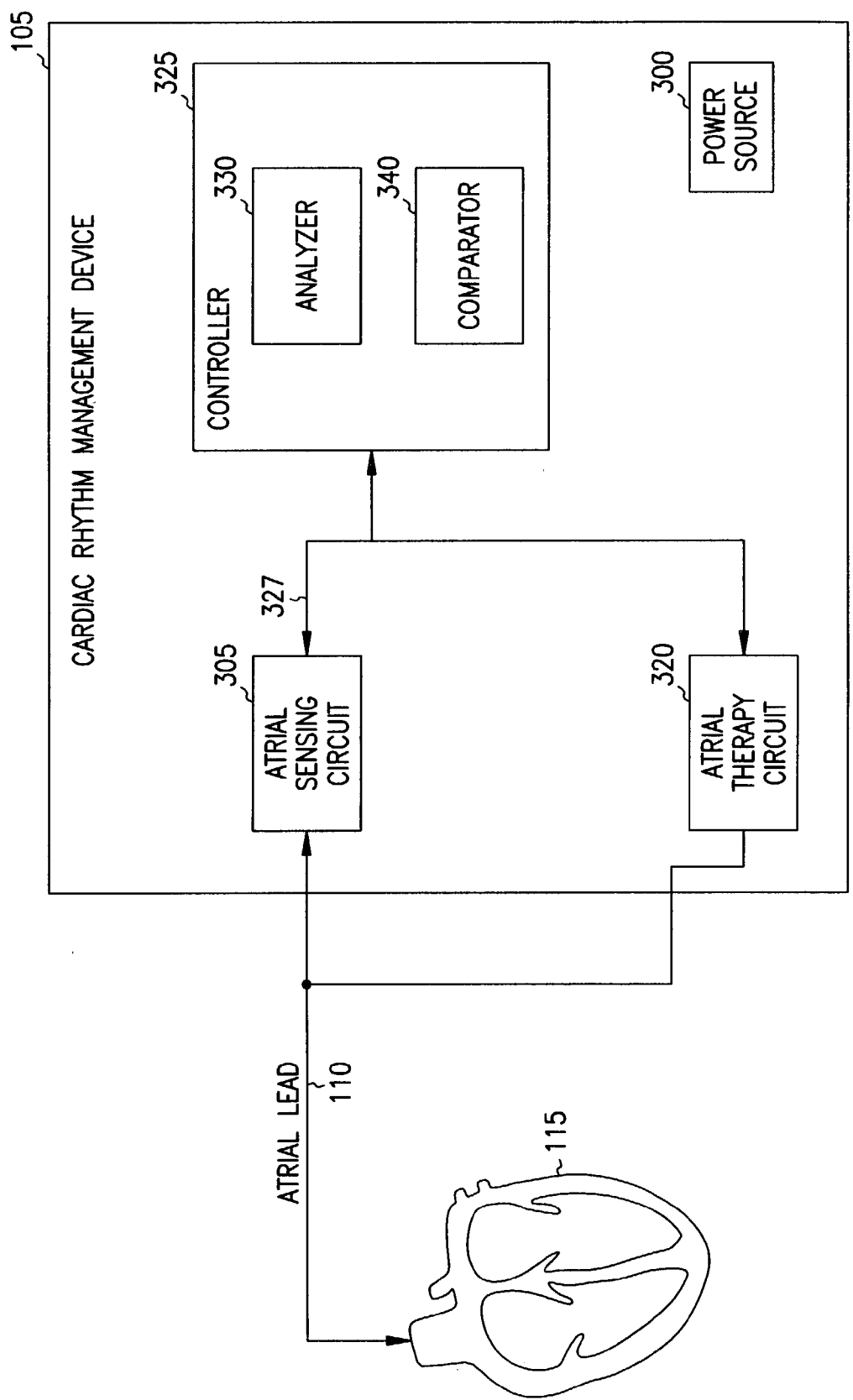
FIG. 3 is a schematic/block diagram illustrating generally one embodiment of portions of a cardiac rhythm management system showing interconnections between major functional components of the present invention.

FIG. 3 is a schematic diagram illustrating generally, by way of example, but not by way of limitation, one embodiment of portions of device 105, which is coupled to a heart 115. Device 105 includes a power source 300, a controller 325, an atrial sensing circuit 305, atrial therapy circuit 320, and a via node/bus 327.

Atrial sensing circuit 305 is coupled by atrial lead 110 to a heart 115 for receiving, sensing, and or detecting electrical atrial heart signals. Such atrial heart signals include atrial activations (also referred to as depolarizations or P-waves) which correspond to atrial contractions. Such atrial heart signals include normal atrial rhythms, and abnormal atrial rhythms including atrial tachyarrhythmias, such as atrial fibrillation, atrial flutter, and other atrial activity. Atrial sensing circuit 305 provides one or more sensed cardiac signals to controller 325, via node/bus 327. Such signals provided to the controller 325 indicate, among other things, the presence of a cardiac arrhythmia. In one embodiment the signals indicate atrial fibrillation and atrial flutter. Controller 325 also controls the delivery of therapy provided by atrial therapy circuit 320 and/or other circuits, as discussed below.

Controller 325 includes various modules, which are implemented either in hardware or as one or more sequences of steps carried out on a microprocessor or other controller. Such modules are illustrated separately for conceptual clarity; it is understood that the various modules of controller 325 need not be separately embodied, but may be combined and/or otherwise implemented, such as in software/firmware.

In general terms, atrial sensing circuits 305 senses electrical signal from a heart tissue in contact with a catheter lead 110 to which the sensing circuit 305 is coupled. Sensed cardiac signal from the sensing circuit 305 is then received and processed by an analyzer 330 of a controller 325 based on an algorithm that uses a serial interval relationship in computing the sensed cardiac signal of the heart 115 to discriminate cardiac arrhythmia. In one embodiment the algorithm discriminates AF from AFL. Based on the outcome of the analyzer 330, comparator 340 of the controller 325 issues a command signal. In one embodiment the comparator 340 issues a command signal to atrial therapy circuit 320, to deliver electrical energy (e.g., pacing and/or defibrillation pulses) to the heart through the lead 110. Controller 325 may include a microprocessor or other controller for execution of software and/or firmware instruction. In one embodiment the software of controller 325 may be modified (e.g., by remote external programmer 105) to provide different parameters, modes, and/or functions for the implantable device 105 or to adapt or to improve performance of device 105.

In one further embodiment, one or more sensors, such as sensor 230, may serve as inputs to controller 325 for adjusting the rate at which pacing or other therapy is delivered to heart 115. One such sensor 230 includes an accelerometer that provides an input to the controller 325 indicating the presence of AF or AFL, for which the controller 325 delivers pacing or defibrillation therapy to a heart 115.

Figure 4A:
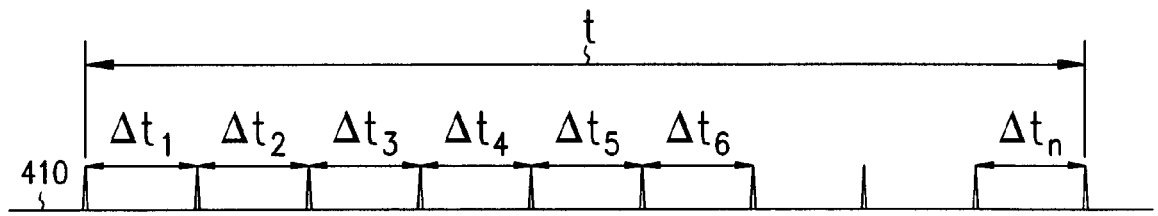
FIG. 4A is a timing diagram illustrating generally one embodiment of atrial flutter responses for a given interval sequence.
Figure 4B:
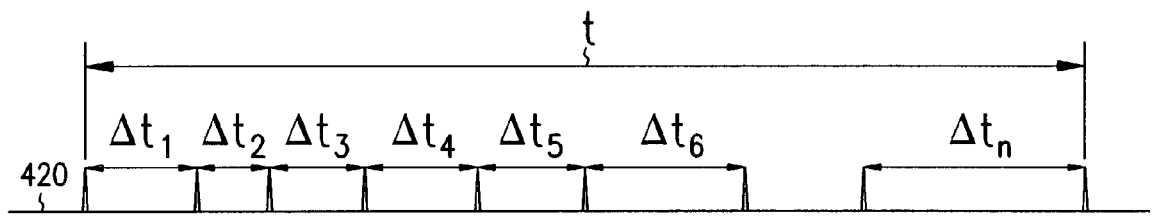
FIG. 4B is a timing diagram illustrating generally one embodiment of atrial fibrillation responses for a given interval sequence.

FIG. 4A is a timing diagram illustrating generally one embodiment of AFL response and FIG. 4B is a graph illustrating generally one embodiment of AF response detected by an atrial or ventricular lead/sensor 110 for a pre-determined interval sequence 't'. FIG. 4B shows one example of AF response exhibiting large intercycle duration variation (high frequency activity) in relation to an average cycle length, and irregular CLs that may change by small or large amounts on an activation-to-activation basis. FIG. 4A shows an example of AFL response exhibiting constant or slowly drifting CLs (low frequency activity) and an average CL greater than or equal to that of AF. Also the FIGS. 4A and 4B shows an example over time, variability of AF CLs and AFL CLs about the average appearing to be similar. It is this irregular nature and difference in CLs between activations of AF versus AFL used in the present invention to detect and differentiate AF from AFL. Also shown in FIGS. 4A and 4B are the cycle lengths ($\Delta t_1 \ldots \Delta t_N$) for a pre-determined interval sequence 't' having 'N' number of cycle lengths. The analyzer 330 receives the sensed cardiac signals and computes the cycle lengths $\Delta t_1, \Delta t_2 \ldots \Delta t_N$. Then the analyzer 330 computes the average cycle length-to-cycle length variation $((1/(N-1))(\Sigma(|\Delta t_1-\Delta t_2|+|\Delta t_2-\Delta t_3|\ldots+|\Delta t_{N-1}-\Delta t_n|)))$. Then the computed values are received by a comparator 340, which compares the computed cycle length-to-cycle length variation with one or more predetermined threshold values, and issues a command signal to a therapy circuit 320 based on the outcome of the comparison. In one embodiment the comparator 340 compares the computed average cycle length with the computed average cycle length-to-cycle length variation, and issues a command signal to a therapy circuit 320 based on the outcome of the comparison. In one embodiment, the comparator issues a command signal to the therapy circuit, if the computed average cycle length-to-cycle length variation is greater than a predetermined threshold value that depends on the average cycle length to provide therapy to a heart. In one embodiment the one or more predetermined threshold values are determined using a receiver operating characteristic (ROC) curve on a database of AF and AFL rhythms representative of the population requiring the discrimination of AF from AFL.

Figure 4C:
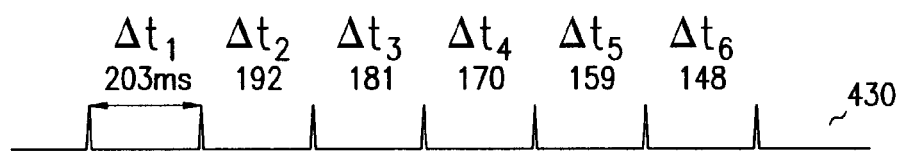
FIG. 4C is a timing diagram illustrating generally another embodiment of atrial flutter responses measured for a given interval sequence.
Figure 4D:
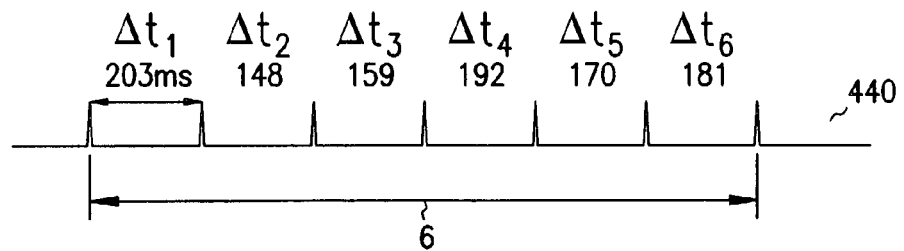
FIG. 4D is a timing diagram illustrating generally another embodiment of atrial fibrillation responses measured for a given interval sequence.

FIG. 4C also illustrates generally, by way of example, but not by way of limitation, one embodiment of AFL response having cycle lengths of 203, 192, 181, 170, 159 and 148 milliseconds for a predetermined interval sequence 't' having 6 cycle lengths. Also shown in FIG. 4D is one embodiment of AF response having cycle lengths 203, 148, 159, 192, 170 and 181 milliseconds for the predetermined interval sequence 't' having 6 cycle lengths. Both of these responses have the same average cycle length of 175.5 milliseconds, and a standard deviation of 20.58 milliseconds (they also have the same minimum, maximum, and range), whereas the cycle length-to-cycle length variation for AF (26.4 milliseconds) is greater than the cycle length-to-cycle length variation for AFL (11 milliseconds). It is clear from this example, that the sequence based measure of high frequency variability between AF and AFL of the present invention proves to be highly specific discriminator when robust atrial interval sequences are available.

Figure 5A:
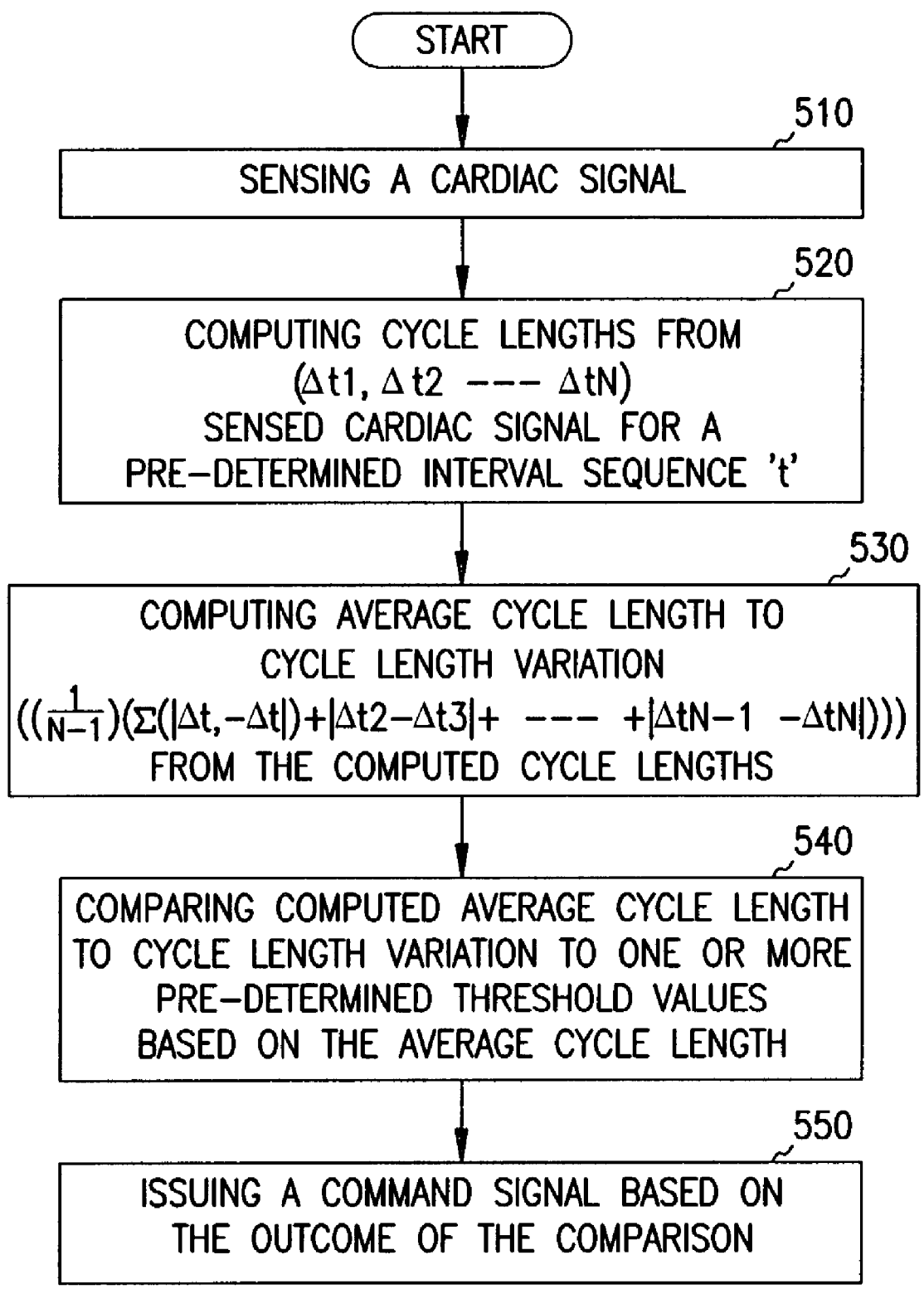
FIG. 5A is flow diagram illustrating generally one embodiment of operation of the cardiac rhythm management device of the present invention.

FIG. 5A is a flow diagram illustrating generally, by way of example, but not by way of limitation, one embodiment of operation of the cardiac rhythm management device including an algorithm that computes average high frequency variability to issue a command signal. Upon sensing a cardiac signal 510, the next step in the process includes computing cycle lengths $(\Delta t_1 \ldots \Delta t_N)$ for a pre-determined interval sequence 't' 520 from the sensed cardiac signal 510. The sensed cardiac signal could be an atrial or ventricular signal. In one embodiment the pre-determined interval sequence is approximately in a range of about 10 to 15 cycle lengths. Then the next step in process includes computing an average cycle length-to-cycle length variability (average high frequency variability) $((1/(N-1))(\Sigma(|\Delta t_1-\Delta t_2|+|\Delta t_2-\Delta t_3|\ldots+|\Delta t_{N-1}-\Delta t_N|))$ 530 from the computed cycle lengths 520. Then the next step includes comparing the computed average high frequency variability with one or more pre-determined threshold values 540. Then the next step includes discriminating a cardiac arrhythmia based on the outcome of the comparison. In one embodiment the next step in the process includes issuing a command signal based on the outcome of the comparison 550.

Figure 5B:
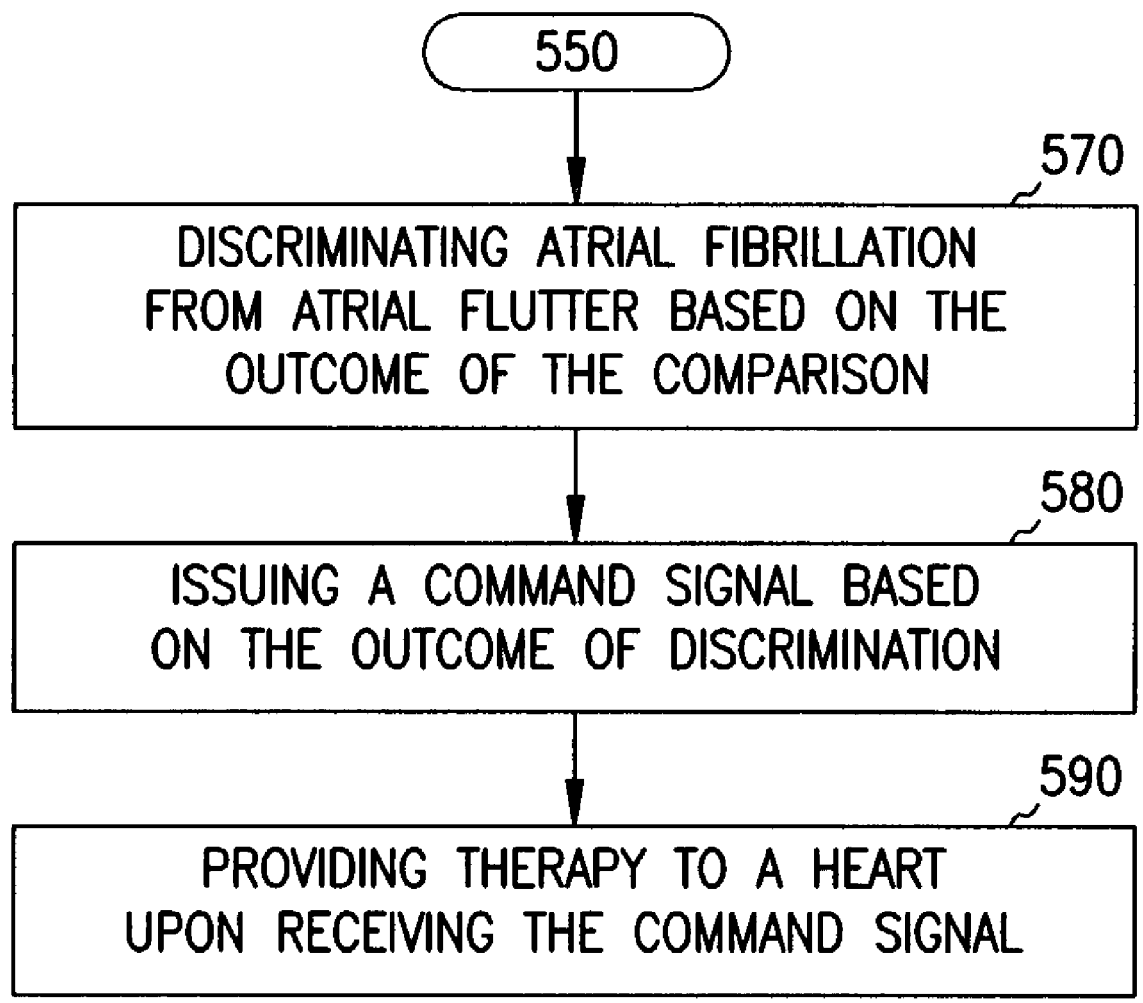
FIG. 5B is a flow diagram similar to FIG. 5A, illustrating generally another embodiment of operation of the cardiac rhythm management device of the present invention.

FIG. 5B is a flow diagram, similar to FIG. 5A, illustrating generally one embodiment of operation of the cardiac rhythm management device including the additional steps of discriminating AF from AFL from a sensed atrial signal 570 based on the outcome of the comparison 540, and issuing a command signal 580 to provide a therapy to a heart 590.

Alternatively additional steps could include discriminating a ventricular fibrillation from a ventricular tachycardia from a sensed ventricular signal based on the outcome of comparison 540, and issuing a command signal to provide the therapy to the heart.

Figure 6:
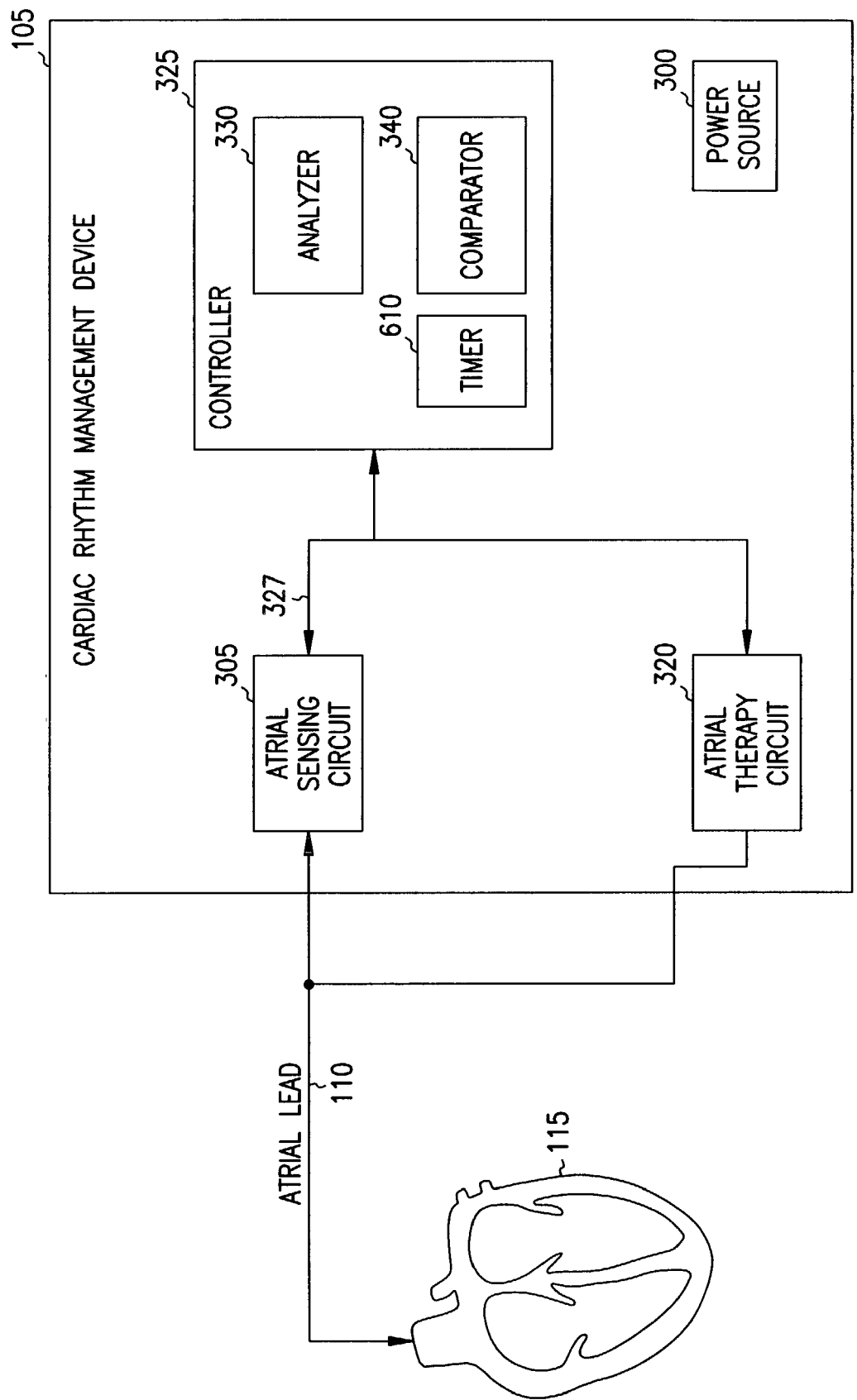
FIG. 6 is a schematic/block diagram, similar to FIG. 3, illustrating generally another embodiment of interconnecting a timer in-addition to what is shown FIG. 3.

FIG. 6 is a schematic drawing, similar to FIG. 3, illustrating generally, by way of example, but not by way of limitation, another embodiment of operation of the cardiac rhythm management device, showing in addition to what is shown in FIG. 3, a timer 610 is included in the controller 325 to introduce a time delay between the command signal issued by the controller 325 and the therapy provided to a heart by the therapy circuit 320. In one embodiment the time delay is introduced (before administering a therapy) to ensure that the command signal issued by the controller is indeed based on a sustained detection of AF from AFL and not based on a spontaneous detection of AF from AFL. In another embodiment the pre-determined delay can be introduced during a ventricular repolarization to avoid inducing a ventricular therapy. In one embodiment the pre-determined time delay is approximately in the range of 1 second to 180 seconds.

Figure 7:
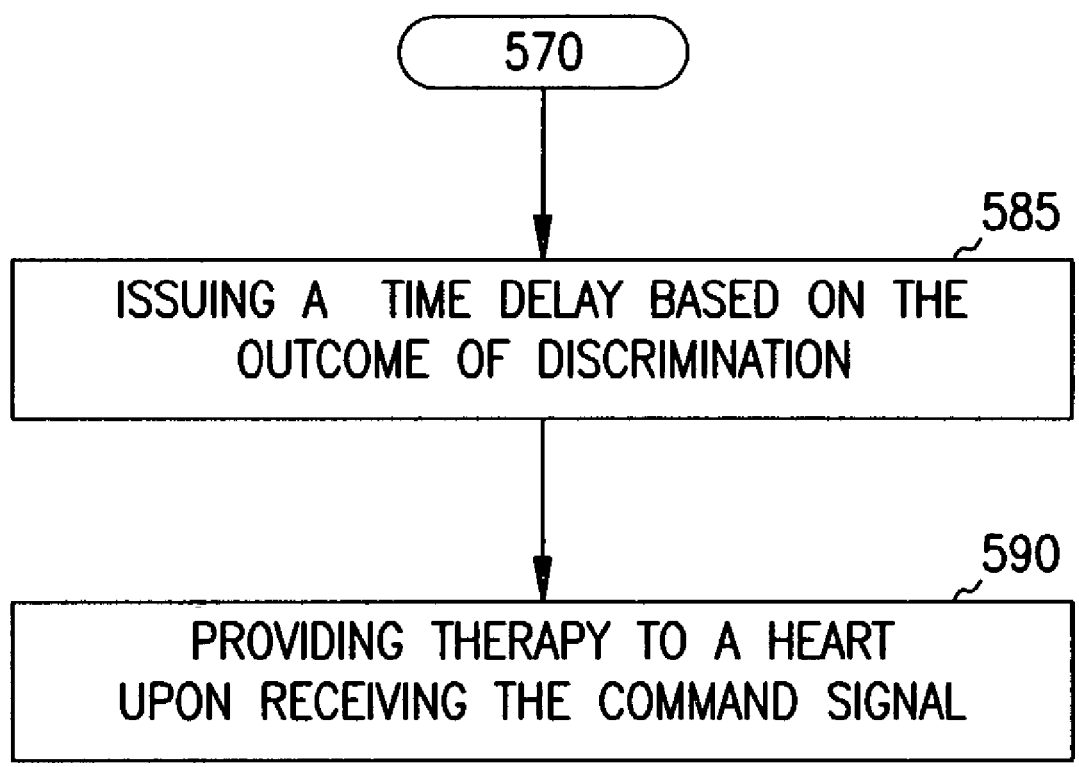
FIG. 7 is a flow diagram, illustrating generally another embodiment of operation of the present invention.

FIG. 7 is a flow diagram, similar to FIGS. 5A and 5B, illustrating generally, by way of example, but not by way of limitation, another embodiment of operation of the cardiac rhythm management device, showing in addition to what is shown in FIGS. 5A and 5B, a time delay 585 introduced between the issuing of a command signal by the controller 325 and the providing of an appropriate therapy to the heart upon receiving the command signal 590.

Figure 8:
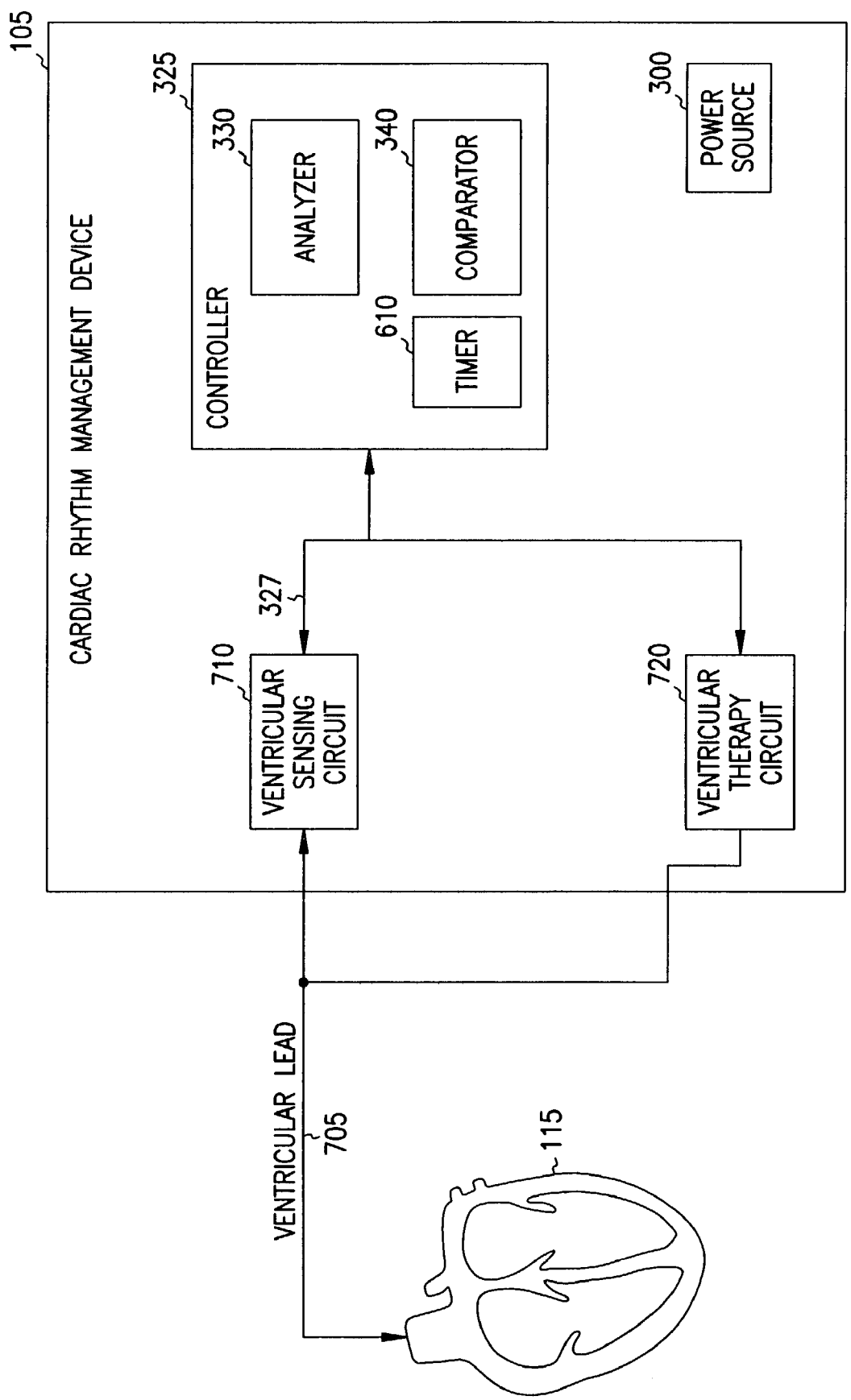
FIG. 8 is a schematic/block diagram illustrating another embodiment of using the present invention in a ventricular chamber.

FIG. 8, is a schematic drawing, similar to FIG. 3, illustrating generally, by way of example, but not by way of limitation, another embodiment of operation of the cardiac rhythm management device, showing ventricular sensing circuit 710 coupled to ventricular lead 705 to a heart 115 for receiving, sensing, and or detecting electrical ventricular heart signals such as, normal ventricular rhythms, ventricular fibrillation, ventricular tachycardia and other ventricular activity. Ventricular sensing circuit 710 provides one or more sensed cardiac signals to controller 325, via node/bus 327. Such signals provided to the controller 325 indicate, among other things, the presence of a cardiac arrhythmia. In one embodiment the signals indicate ventricular fibrillation from ventricular tachycardia. Controller 325 also controls the delivery of therapy provided by ventricular therapy circuit 720 and/or other circuits, as discussed below.

Controller 325 includes various modules, which are implemented either in hardware or as one or more sequences of steps carried out on a microprocessor or other controller. Such modules are illustrated separately for conceptual clarity; it is understood that the various modules of controller 325 need not be separately embodied, but may be combined and/or otherwise implemented, such as in software/firmware.

In general terms, atrial sensing circuits 710 senses electrical signal from a heart tissue in contact with a catheter lead 705 to which the sensing circuit 305 is coupled. Sensed cardiac signal from the sensing circuit 710 is then received and processed by an analyzer 330 of a controller 325 based on an algorithm that uses a serial interval relationship in computing the sensed cardiac signal of the heart 115 to discriminate cardiac arrhythmia. In one embodiment the algorithm discriminates ventricular fibrillation from ventricular tachycardia.

A timer 610 is included in the controller 325 to introduce a time delay between the command signal issued by the controller 325 and the therapy provided to a heart by the ventricular therapy circuit 720. In one embodiment the time delay is introduced (before administering a therapy) to ensure that the command signal issued by the controller is indeed based on a sustained detection of a ventricular fibrillation from a ventricular tachycardia and not based on a spontaneous detection of the ventricular fibrillation from the ventricular tachycardia.

Figure 9:
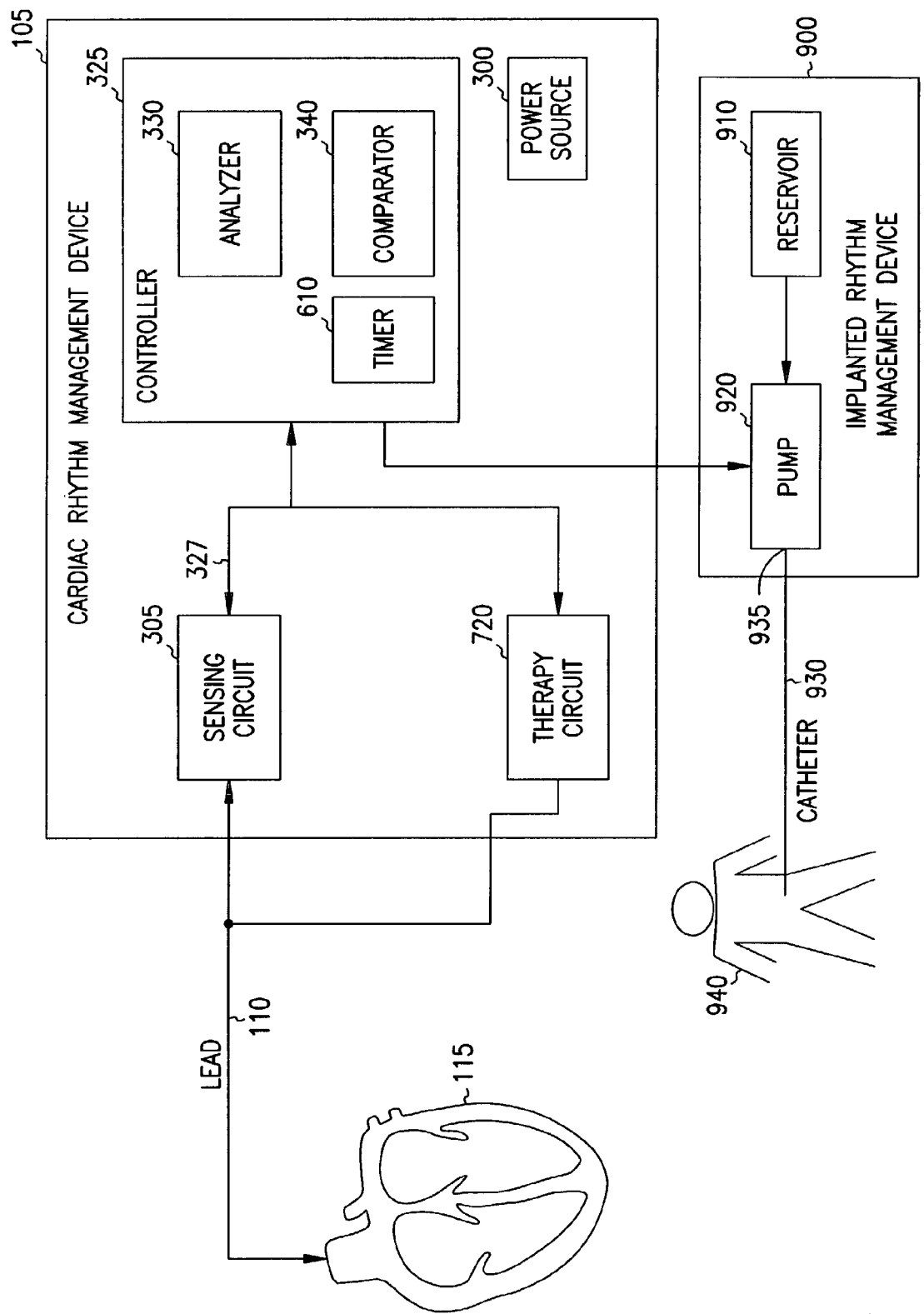
FIG. 9 is a schematic/block diagram illustrating another embodiment of interconnecting an implanted rhythm management device in addition to what is shown in FIG. 6.

FIG. 9, is a schematic drawing, similar to FIG. 6, illustrating generally, by way of example, but not by way of limitation, one embodiment of an implanted rhythm management device 900, coupled to the cardiac rhythm management device 325. The implanted rhythm management device 900 includes a reservoir 910 to hold a drug, and a pump 920 coupled to the reservoir 910, and a catheter 930 coupled to the pump on end 935 and disposed inside a patient's body on the other end 940, administers the drug to the patient's body upon receiving a command signal from the controller 325. In one embodiment the timer 610 introduces a predetermined delay for administering the drug upon receiving the command signal from the comparator 340. In one embodiment the pre-determined delay is approximately in the range of about 1 second to 180 seconds. In one embodiment the implanted rhythm management device 900 and the cardiac rhythm management device 325 are integrated into a single implantable unit.

CONCLUSION

The above-described system provides, among other things, a cardiac rhythm management system for detecting atrial arrhythmia and then to discriminate AF from AFL from the detected atrial arrhythmia. The present system provides, among other things, a highly reliable technique for detecting AF and for discriminating AF from AFL. The present technique allows for reduced computation (in comparison to current techniques), and increased sensitivity and specificity in discriminating between AF and AFL. This technique may also have other applications, such as in discriminating ventricular tachycardias from ventricular fibrillation.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method including:
    sensing a cardiac signal; and
    discriminating a cardiac arrhythmia based on comparison of two or more pre-determined interval sequences of the sensed cardiac signal by:
    computing a central tendency cycle length-to-cycle length variation for a pre-determined interval sequence of the sensed cardiac signal;
    comparing the computed central tendency cycle length-to-cycle length variation with one or more pre-determined threshold values; and
    determining atrial fibrillation from atrial flutter based on the outcome of the comparison.

2. The method of claim 1, where discriminating further comprises:
    computing an average cycle length-to-cycle length variation for a pre-determined interval sequence;
    comparing the computed average cycle length-to-cycle length variation with one or more pre-determined threshold values; and
    issuing a command signal based on the outcome of the comparison.

3. The method of claim 2, where computing of average cycle length-to-cycle length variation further includes:
    computing cycle lengths ($\Delta t_1, \Delta t_2 \ldots \Delta t_N$) from the sensed cardiac signal for a pre-determined interval sequence; and
    computing average cycle length-to-cycle length variation $((1/(N-1))\ (\Sigma(|\Delta t_1-\Delta t_2|+|\Delta t_2-\Delta t_3|\ldots +|\Delta t_{N-1}-\Delta t_N|)))$ from the computed cycle lengths for the pre-determined interval sequence.

4. The method of claim 2, further includes providing electrical energy to at least one electrode upon receiving the command signal.

5. The method of claim 2, further includes providing a cardiac therapy to a heart upon receiving the command signal.

6. The method of claim 2, where sensing a cardiac signal includes sensing atrial signals.

7. The method of claim 2, further including activating an implanted device to administer a drug therapy to the heart upon receiving the command signal.

8. A method including:
    sensing a cardiac signal;
    computing cycle lengths ($\Delta t_1, \Delta t_2 \ldots \Delta t_N$) from the detected cardiac signal for a pre-determined interval sequence;
    computing average cycle length-to-cycle length variation from the computed cycle lengths;
    comparing one or more predetermined threshold values with the computed average cycle length-to-cycle length;
    introducing a time delay to provide therapy to a heart based on the outcome of the comparison; and
    providing the therapy to a heart.

9. A method comprising:
    sensing a cardiac signal;
    computing cycle lengths from the sensed cardiac signal for the pre-determined number of sequential cardiac cycles;
    computing cycle length-to-cycle length variations from the computed cycle lengths; and
    computing a central tendency cycle length-to-cycle length variation from the computed cycle length-to-cycle length variations
    discriminating between ventricular fibrillation and ventricular tachycardia based on the outcome of the comparison.

10. The method of claim 9, wherein computing the central tendency cycle length-to-cycle length variation comprises computing an average cycle length-to-cycle length variation.

11. The method of claim 9, wherein computing the central tendency cycle length-to-cycle length variation comprises computing a median cycle length-to-cycle length variation.

12. The method of claim 9, farther comprising selecting a defibrillation therapy if ventricular fibrillation is detected.

13. The method of claim 12, further comprising:
    starting a pre-determined time delay if the ventricular fibrillation is detected;
    determining whether the ventricular fibrillation sustains; and
    stopping the pre-determined time delay if the ventricular fibrillation does not sustain.

14. The method of claim 13, further comprising providing defibrillation therapy to the heart if the pre-determined time delay is completed without being stopped.

15. The method of claim 14, wherein the pre-determined time delay is at least about one second.

16. The method of claim 14, wherein the pre-determined time delay is less than about 180 seconds.

17. The method of claim 9, further comprising selecting a pacing therapy if ventricular tachycardia is detected.

18. A method, comprising:
sensing an atrial signal;
computing cycle lengths from the sensed atrial signal for a pre-determined number of sequential cardiac cycles;
computing cycle length-to-cycle length variations from the computed cycle lengths;
computing an average cycle length-to-cycle length variation from the computed cycle length-to-cycle length variations;
comparing the computed average cycle length-to-cycle length variation with one or more pre-determined threshold values;
discriminating an atrial fibrillation from an atrial flutter based on an outcome of the comparing; and
providing a defibrillation therapy if the atrial fibrillation is discriminated.

19. A method, comprising:
sensing a ventricular signal;
computing cycle lengths from the sensed ventricular signal for a pre-determined number of sequential cardiac cycles;
computing cycle length-to-cycle length variations from the computed cycle lengths;
computing an average cycle length-to-cycle length variation from the computed cycle length-to-cycle length variations;
comparing the computed average cycle length-to-cycle length variation with one or more pre-determined threshold values;
discriminating a ventricular fibrillation from a ventricular tachycardia based on an outcome of the comparing; and
providing a therapy based on an outcome of the discriminating.

* * * * *

UNITED STATES PATENT AND TRADEMARK OFFICE
CERTIFICATE OF CORRECTION

PATENT NO. : 7,177,682 B2
APPLICATION NO. : 10/218944
DATED : February 13, 2007
INVENTOR(S) : Lovett It is certified that error appears in the above-identified patent and that said Letters Patent is hereby corrected as shown below:

On the face page, in field (56), under "U.S. Patent Documents", in column 1, line 1, delete "O'Hanion," and insert -- O'Hanlon, --, therefor.

On the face page, in field (56), under "'U.S. Patent Documents", in column 1, line 2, delete "O'Hanion" and insert -- O'Hanlon, --, therefor.

In column 10, line 59, in Claim 12, delete "farther" and insert -- further --, therefor.

Signed and Sealed this

First Day of May, 2007

JON W. DUDAS
*Director of the United States Patent and Trademark Office*